United States Patent [19]

Maignan et al.

[11] Patent Number: 5,154,918
[45] Date of Patent: Oct. 13, 1992

[54] COSMETIC COMPOSITION FOR USE IN PERMANENT DEFORMATION OF HAIR CONTAINS AS A REDUCING AGENT A DERIVATIVE OF N-(MERCAPTO ALKYL) SUCCINAMIC ACID OR OF N-(MERCAPTO ALKYL) SUCCINIMIDE

[75] Inventors: Jean Maignan, Tremblay Les Gonesse; Gérard Malle, Villiers Sur Morin, both of France

[73] Assignee: L'Oreal, Paris, France

[21] Appl. No.: 721,336

[22] Filed: Jul. 1, 1991

[30] Foreign Application Priority Data

Jul. 2, 1990 [FR] France ................. 90 08343

[51] Int. Cl.$^5$ .............................. A61K 7/09
[52] U.S. Cl. ....................... 424/72; 424/71; 548/545
[58] Field of Search ............. 424/71, 72; 514/784, 514/974; 548/545; 560/190; 568/63, 69

[56] References Cited

U.S. PATENT DOCUMENTS

| | | | |
|---|---|---|---|
| 2,615,828 | 10/1952 | Haefele | 424/71 |
| 2,736,323 | 2/1956 | McDonough | 424/72 |
| 3,071,515 | 1/1963 | Wehr | 424/72 |
| 3,768,490 | 10/1973 | Kalopissis et al. | 424/72 |
| 4,532,950 | 8/1985 | Lang et al. | 424/72 |
| 4,888,138 | 12/1989 | Laurenzo | 564/555 |

FOREIGN PATENT DOCUMENTS 0354835 2/1990 European Pat. Off. .
1303214 7/1972 France .

OTHER PUBLICATIONS

Patent Abstracts of Japan, vol. 12, No. 59 (C-478) [2906], Feb. 1988.
Patent Abstracts of Japan, vol. 12, No. 405 (C-539) [3252], Oct. 1988.

French Search Report of FR 90 08343.

Primary Examiner—Thurman K. Page
Assistant Examiner—D. Colucci
Attorney, Agent, or Firm—Cushman, Darby & Cushman

[57] ABSTRACT

A cosmetic composition for the first stage of an operation for the permanent deformation of hair contains, as a reducing agent, a compound having the formula

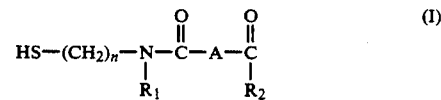

wherein, n is 2 or 3; A represents a divalent radical selected from (i) —$(CH_2)_m$—, wherein m is 2 or 3, (ii)

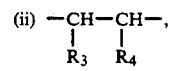

wherein $R_3$ and $R_4$, each independently, represent alkyl having 1-4 carbon atoms, or $R_3$ and $R_4$ together with the adjacent carbon atoms form a cyclohexane ring, and (iii)

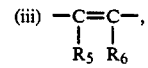

wherein $R_5$ and $R_6$, each independently, represent hydrogen, alkyl having 1-4 carbon atoms, or $R_5$ and $R_6$ together with the adjacent carbon atoms form a benzene ring; $R_1$ represents hydrogen; $R_2$ represents hydroxy, or $R_1$ and $R_2$ taken together form a simple bond, and the salts of an organic or mineral base of said compound in free acid form.

19 Claims, No Drawings

COSMETIC COMPOSITION FOR USE IN PERMANENT DEFORMATION OF HAIR CONTAINS AS A REDUCING AGENT A DERIVATIVE OF N-(MERCAPTO ALKYL) SUCCINAMIC ACID OR OF N-(MERCAPTO ALKYL) SUCCINIMIDE

The present invention relates to a cosmetic reducing composition for the first stage of a permanent deformation of hair operation, containing, as a reducing agent, a derivative of N-(mercapto alkyl) succinamic acid or of N-(mercapto alkyl) succinimide or their homologs and its use in a process for the permanent deformation of hair.

The technique to effect the permanent deformation of hair consists, in a first stage, effecting the opening of the disulfide bonds of keratin (cystine) using a composition containing a reducing agent (reduction step), and then, after having preferably rinsed the hair, to reconstitute in a second step the said disulfide bonds by applying, on the hair under tension, an oxidizing composition (oxidation step, also called fixation) so as to give to the hair the form desired. This technique permits indifferently to effect either a waving of the hair, or uncurling or uncrisping of the hair.

Compositions to effect the first stage of a permanent waving operation are generally provided in the form of lotions, creams, gels or powders to be diluted in a liquid support and contain, preferably a mercaptan as the reducing agent.

Among these latter, those currently employed are thioglycolic acid and thiolactic acid or a mixture of these acids, as well as their esters, for example, the monothioglycolate of glycerol or glycol.

These reducing agents which are particularly effective in reducing the disulfide bonds of keratin include, principally, thioglycolic acid which can be considered as the product of choice in permanent waving operations. It provides a reduction in the amount of about 50%.

These reducing agents exhibit, however, a major disadvantage since they emit bad odors, characteristic of sulfur compounds, which at times render the permanent waving operation distressing, not only for persons who undergo such operation, but also for persons effecting such an operation.

With a view to reducing this disadvantage, a perfume is generally employed to mask the odors.

After significant studies, it has now been observed, in a quite unexpected and surprising manner, that by using a new class of derivatives of N-(mercapto alkyl) succinamic acid or of N-(mercapto alkyl) succinimide or their homologs, it was possible to remedy certain disadvantages of state of the art reducing agents.

The reducing agents of the compositions according to the present invention exhibit in effect good reducing properties and are practically odor free.

The present invention thus relates to, as a new industrial product, a cosmetic composition for the first stage of a permanent deformation of hair operation containing, in an appropriate cosmetic vehicle, as a reducing agent, at least one derivative of N-(mercapto alkyl) succinamic acid or of N-(mercapto alkyl) succinimide or one of their homologs having the following formula:

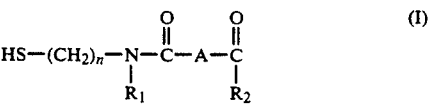

wherein
n is 2 or 3,
A represents a divalent radical selected from (i) $-(CH_2)_m-$, wherein m is 2 or 3, (ii)

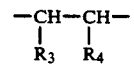

wherein $R_3$ and $R_4$, each independently, represent alkyl having 1–4 carbon atoms, or $R_3$ and $R_4$ together with the adjacent carbon atoms form a cyclohexane ring, and (iii)

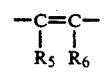

wherein $R_5$ and $R_6$, each independently, represent hydrogen, alkyl having 1–4 carbon atoms or $R_5$ and $R_6$ together with the adjacent carbon atoms form a benzene ring,
$R_1$ represents hydrogen and
$R_2$ represents hydroxy or
$R_1$ and $R_2$ taken together form a simple bond, and the salts of an organic or mineral base of the said compounds in free acid form.

When the compounds of general formula (I) above are provided in the form of salts, it is a question more particularly of an ammonium salt, a secondary or tertiary amine salt or again a salt of an alkali metal or alkaline earth metal.

In general formula (I) above, when the $R_3$ and $R_4$ radicals together with the adjacent carbon atoms form a cyclohexane ring, the corresponding divalent radical is the 1,2-cyclohexylidene radical.

Moreover, when radicals $R_5$ and $R_6$ together with the adjacent carbon atoms form a benzene ring, the corresponding divalent radical is the O-phenylene radical.

By alkyl having 1–4 carbon atoms is meant a methyl, ethyl, propyl, isopropyl or butyl radical.

Among the compounds of formula (I) above in which $R_1$ represents hydrogen and $R_2$ represents hydroxy the following can principally be mentioned:
N-(2-mercapto ethyl) succinamic acid,
N-(3-mercapto propyl) succinamic acid,
N-(2-mercapto ethyl) hexahydrophthalamic acid,
N-(3-mercapto propyl) hexahydrophthalamic acid,
N-(2-mercapto ethyl) phthalamic acid,
N-(3-mercapto propyl) phthalamic acid,
N-(2-mercapto ethyl) glutaramic acid,
N-(3-mercapto propyl) glutaramic acid and
N-(2-mercapto ethyl) maleamic acid.

Among the compounds of formula (I), above, in which $R_1$ and $R_2$, taken together, form a simple bond, the following can principally be mentioned:
N-(2-mercapto ethyl) succinimide,
N-(3-mercapto propyl) succinimide,
N-(2-mercapto ethyl) glutarimide,
N-(3-mercapto propyl) glutarimide,
N-(2-mercapto ethyl) hexahydrophthalimide and N-(3-mercapto propyl) hexahydrophthalimide.

Certain ones of the compounds of formula (I) are known while others are new. Concerning these latter there will be given below various methods how to obtain them as well as several examples of their preparation.

In the compositions according to the present invention the reducing agent of general formula (I) is generally present in an amount ranging from 2 to 20 percent and preferably form 5 to 10 percent by weight based on the total weight of the reducing composition.

The pH of the composition is preferably between 4.5 and 11, and more particularly between 6 and 10 and the pH is obtained using an alkaline agent such as, for example, ammonia, monoethanolamine, diethanolamine, triethanolamine, an alkaline or ammonium carbonate or bicarbonate, an alkaline hydroxide or using an acidifying agent such as, for example, hydrochloric acid, acetic acid, lactic acid, oxalic acid or boric acid.

The reducing composition can also contain other known reducing agents such as, for example, thioglycolic acid, glycerol or glycol monothioglycolate, cysteamine and its $C_1$–$C_4$ acyl derivatives, such as N-acetylcysteamine or N-propionyl cysteamine, cysteine, N-acetyl cysteine, N-mercapto alkylamides of sugars such as N-(2-mercapto ethyl) gluconamide, β-mercaptopropionic acid and its derivatives, thiolactic acid, thiomalic acid, pantetheine, thioglycerol, the sulfites and bisulfites of an alkali metal or alkaline earth metal, N-(mercaptoalkyl) ω-hydroxyalkylamides described in EP patent application 354,835, the N-mono or N,N-dialkylmercapto 4-butyramides described in EP patent application 368,763, and the aminomercapto alkylamides described in EP patent application 403,267.

The reducing composition can also contain various ingredients such as, for example, cationic polymers such as those employed in the composition of French Patents Nos. 79.32078, 80.26421 and 89.16273 or even cationic polymers of the ionene type, such as those used in the compositions of French Patent No. 82.17364, softening agents and principally quaternary ammonium derivatives of lanolin, protein hydrolyzates, waxes, opacifying agents, perfumes, dyes, non-ionic or cationic surface active agents, treating agents or even penetration agents such as urea, pyrrolidone or thiomorpholinone.

The reducing composition according to the invention can also be of the exothermic type, i.e., provoking a certain amount of heat during application to the hair, which is agreeable to the person undergoing the first stage of the permanent or uncurling of the hair.

The vehicle of the composition according to the invention i preferably water or a hydroalcoholic solution of a lower alcohol such as ethanol, isopropanol or butanol.

When the compositions are intended for a hair uncurling or uncrisping operation, the reducing composition is preferably in the form of a cream so as to maintain the hair as rigid or stiff as possible. These creams are provided in the form of "heavy" emulsions, for example, those based on glycerol stearate, glycol stearate, self-emulsifying waxes, fatty alcohols, etc. Liquids or gels containing thickening agents, such as carboxyvinyl polymers or copolymers which "glue" the hair can also be employed so as to maintain the hair in a smooth position during the setting period.

The compositions according to the invention can also be, according to a particular embodiment, under the form called "self-neutralizing" or even "self-regulated" and in this case the reducing compound of formula (I) is combined with at least one disulfide either known for its use in a reducing composition for permanent self-neutralization, or derived from a compound of formula (I) which can be represented by the following general formula

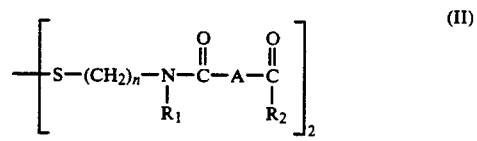

wherein n, $R_1$, $R_2$ and A have the same meanings as those given for formula (I).

Among the known disulfides, there can principally be mentioned dithioglycolic acid, dithioglycerol, cystamine, N,N-diacetylcystamine, cystine, pantetheine and the disulfides of N-(mercaptoalkyl) ω-hydroxyalkylamides described in EP patent application 354,835, the disulfides of N-mono or N,N-dialkylmercapto 4-butyramides described in EP patent application 368,763 and the disulfides of aminomercaptoalkylamides described in EP patent application 403,267.

Among the disulfides of formula (II) the following can principally be mentioned:
bis[N-(3-carboxy propionyl)N-ethyl]disulfide,
bis[N-(2-carboxy cyclohexane carbonyl)N-ethyl]disulfide and
bis[N-ethyl succinimide]disulfide.

The disulfide is generally present in the compositions in a molar amount with respect to the thiol of formula (I) ranging from 0.5 to 2.5 and preferably from 1 to 2 (see U.S. Pat. No. 3,768,490).

The present invention also relates to a process for the permanent deformation of hair comprising, in a first stage, reducing the disulfide bonds of keratin by applying to the hair for a period of about 5 to 60 minutes, a reducing composition, such as defined above, and then in a second stage reforming the said bonds by applying to the hair an oxidizing composition or optionally by letting the oxygen of the air act on the hair.

The present invention also relates to a process for waving the hair in which a reducing composition, such as defined above, is applied to wet hair, previously rolled on rollers having a diameter of 4 to 20 mm. The composition can optionally be applied gradually while rolling up the hair.

The reducing composition is then permitted to act on the hair for a period of time ranging from 5 to 60 minutes and preferably 5 to 30 minutes. The hair is then thoroughly rinsed, after which there is applied to the rolled up hair, an oxidizing composition so as to reform the disulfide bonds of the keratin during a setting period of 2 to 10 minutes. After having removed the rollers the hair is thoroughly rinsed.

The oxidation composition, or oxidizing agent, is of the type currently employed and contains as the oxidizing agent $H_2O_2$, an alkaline bromate, a persalt, a polythionate or a mixture of an alkaline bromate and a persalt. This oxidation can be immediate or deferred. The concentration of $H_2O_2$ can vary from 1 to 20 volumes and preferably form 1 to 10 volumes; the concentration of alkaline bromate, from 2 to 12 percent; and that of persalt from 0.1 to 15 percent by weight based on the total weight of the oxidation composition. The pH of the oxidation composition is generally between 2 and 10.

The present invention also relates to a process for uncurling or uncrisping the hair which comprises applying to the hair a reducing composition, according to the invention, submitting the hair to a mechanical deformation so as to fix the hair in a new form, by smoothing the hair with a comb having large teeth or with the back of the comb or with the hand. After a setting period of 5 to 60 minutes, particularly 5 to 30 minutes, the hair is again smoothed and then carefully rinsed. The oxidation or fixing composition is then applied to the hair and left in contact therewith for about 2 to 10 minutes. The hair is then thoroughly rinsed.

The compounds of general formula (I) are prepared in accordance with known processes.

The derivatives of N-(mercapto alkyl) succinamic acid or their homologs, i.e. compounds of formula I wherein $R_1=H$ and $R_2=OH$, are obtained by reacting a mercapto alkylamine (1) with an anhydride of formula (2) in accordance with the following reaction scheme:

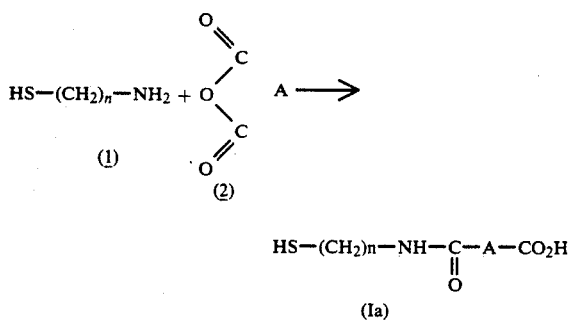

The mercapto alkylamines (1) employed are either 2-mercapto ethylene amine or cysteamine (n=2), or 3-mercapto propylamine (n=3).

The anhydrides (2) are succinic anhydride, maleic anhydride, 1,2-cyclohexane dicarboxylic anhydride, phthalic anhydride, methyl succinic anhydride or glutaric anhydride.

The reaction of opening the anhydride (2) is generally carried out under an inert atmosphere in an alcohol such as methanol, ethanol, isopropanol or butanol, and according to the boiling point of the latter and the ease with which the acids of formula (Ia) cyclize, at a temperature between 0° and 110° C.

It can be advantageous to employ salts of the mercapto alkylamines (1), principally the hydrochlorides, and in this case the preferred solvent is ethanol and the base employed to free the amine is a tertiary amine. It can be advantageously to add an excess of amine, this in order to salify in proportion the acid (Ia) formed and thus to limit cyclization.

When the mercapto alkylamines (1) are in free amine form, it can be advantageous not to use any solvent and to mix in stoichiometric proportions the mercapto alkylamine and the anhydride, and to bring the mixture to a temperature between 20° and 100° C.

When the mercapto alkylamine is cysteamine, it is desirable to operate in an autoclave so as to eliminate problems of sublimation.

The evolution of the reaction is followed by dosage of the non transformed mercapto alkylamine. When the reaction time is too long, it can be advantageous to use an excess of the mercapto alkylamine that is removed at the end of the reaction by filtration of the mixture on a sulfonic acid resin.

The derivatives of N-(mercapto alkyl)succinimide or their homologs, i.e. compounds of formula (I) wherein $R_1$ and $R_2$, taken together, form a simple bond, are obtained by dehydration of the succinamic acid of formula (Ia).

In order to effect the dehydration reaction, preferably an aromatic solvent is selected which forms an azeotrope with the water formed during the course of the reaction, which has a sufficiently high boiling point, such as toluene or xylene. In this case a water separator (Dean Stark) is employed, and it is then easy to follow the evolution of the reaction by measuring the volume of water removed.

The N-(mercapto alkyl) succinimides or their homologs can also be obtained starting with the mercapto alkylamine (1) and anhydride (2) in the presence or not of a solvent, with the intermediate isolation of the succinamic acid derivative (Ia), the cyclization being effected by prolonged heating by placing the mixture under reduced pressure when a reaction solvent is not employed.

If during the course of the reactions a certain amount of thiol is oxidized to the corresponding disulfide, the reaction mixture is then diluted by twice its volume with water and is stirred in the presence of a mixture of sulfonic resin and zinc powder for 3 to 10 hours.

The majority of the disulfide being reduced, the mixture is then filtered and one obtains a solution of the expected product is obtained which can be used directly.

In the case of self-neutralizing compositions, the reaction mixture containing a certain amount of thiol oxidized into disulfide can be employed without proceeding to the reduction of the disulfide. In certain cases, depending upon the nature of the anhydride (2) employed, the succinamic acids (Ia) easily cyclize and a mixture of the acid and the corresponding imide is obtained.

The disulfides (II) according to the invention can be obtained by oxidation of the compounds of formula (I) either by free air or preferably by using, for example, $H_2O_2$ in the optional presence of ferrous ions.

The disulfides (II) can also be obtained by the reaction of a disulfide of formula (3) with an anhydride (2) according to the following reaction scheme:

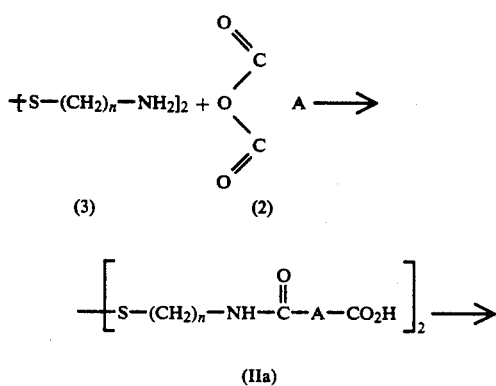

-continued

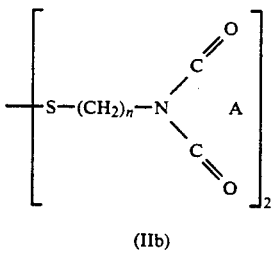

(IIb)

The disulfides (IIa) lead on prolonged heating to disulfides of formula (IIb).

The present invention also related to as a new industrial product compounds having the following general formulas (III) and (IV)

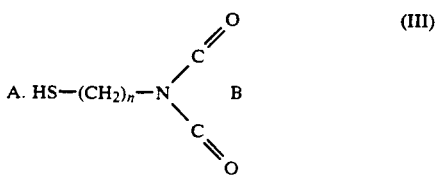

wherein
n is 2 or 3, and
B represents a divalent radical selected from the group consisting of:
(i) —$(CH_2)_3$—
(ii) 1,2-cyclohexylidene, and
(iii) —CH=CH— when in this latter case n is 3, and their corresponding disulfides.

wherein
n is 2 or 3,
(a) when n is 2,
Z represents 1,2-cyclohexylidene
(b) when n is 3,
Z is a divalent radical selected from the group consisting of
(i) —$(CH_2)_m$— wherein m is 2 or 3,
(ii) —CH=CH—,
(iii) 1,2-cyclohexylidene, and
(iv) O-phenylene, and
their corresponding disulfides, as well as the corresponding disulfide when n is 2 and Z represents o-phenylene.

There are now given, an illustration and without any limiting character, several examples of the preparation of compounds of formulas (I) and (II) as well as several examples of reducing compositions according to the invention and their use in a process for the permanent deformation of hair.

EXAMPLE I

Preparation of N-(2-mercapto ethyl) succinamic acid (a) Starting with cysteamine hydrochloride Into a reactor there are introduced under an inert atmosphere 114 g of cysteamine hydrochloride to which are slowly added, with mechanical stirring and at ambient temperature, 133 cm³ of triethanolamine dissolved in 180 cm³ of absolute ethanol. A slight isothermicity is observed and then 100 g of succinic anhydride are introduced so as to maintain the medium at a temperature close to 40° C. The mixture is then stirred for 3 hours at ambient temperature and left overnight under an inert atmosphere. The transformation of anhydride is followed by vapor phase chromatography (V.P.C.) and that of the starting amine by dosage of the amount of remaining amine. After 3 hours of reaction, there remains practically no more starting product. The salt is removed by filtration and the filtrate is concentrated under reduced pressure. 170 g of a crude product are obtained which crystallizes in the form of a pasty solid at ambient temperature. This product is stirred under an inert atmosphere in 200 cm³ of 1,2-dichloroethane that is progressively heated to boiling. After return to ambient temperature, two liquid phases are observed and are cooled to 0° C. for 4 hours. A solid which forms is filtered, washed three times with 100 cm³ of ethyl ether and then dried under reduced pressure. 125 g of white powder are obtained and recrystallized hot in ethyl acetate. After cooling, filtering and drying under a vacuum at 45° C., 100 g of N-(mercapto ethyl) succinamic acid are obtained in the form of a white solid having a melting point of 82° C. The NMR ¹H 250 MHz spectrum conforms to the anticipated structure. Dosages of the thiol and carboxylic acid functions are greater than 95% theory.

Elemental analysis: $C_6H_{11}NO_3S$:
Calculated: C: 40.66, H: 6.26, N: 7.90, O: 27.08, S: 18.09.
Found: 40.79, H: 6.24, N: 7.91, O: 27.24, S: 17.89.

(b) Starting with cysteamine

A mixture of 5 g of cysteamine and 6 g of succinic anhydride is stirred under an inert atmosphere at a temperature of about 100° C. The transformation of the starting products is practically total one-half hour after the beginning of the reaction. The mixture is dissolved in 50 cm³ of water to which are added, with stirring, 5 g of sulfonic acid resin and 3 g of zinc powder to transform the disulfide present in the mixture. The resin is removed by filtration and the filtrate is concentrated under reduced pressure. After drying, 9 g of N-(2-mercapto ethyl) succinamic acid are obtained whose characteristics are identical to those of the acid obtained following the procedure of section (a), above.

EXAMPLE II

Preparation of N-(2-mercapto ethyl) succinimide (a) Starting with cysteamine

There is progressively heated, under an inert atmosphere, a mixture of 5 g of cysteamine and 6 g of succinic anhydride stirred for 6 hours to a temperature of 130° C.

About one-half hour is necessary for the complete transformation of the succinic anhydride (V.P.C.). At this stage, to facilitate the cyclization reaction, the reaction mixture is placed under reduced pressure and the evolution of the reaction mixture is followed by acidimetric dosage of the nontransformed N-(2-mercapto ethyl) succinamic acid. At the end of the reaction, the mixture is cooled and 7 g of crude product are obtained and dissolved in 50 cm³ of water to which are added, with stirring, 10 g of sulfonic acid resin. After stirring for one hour, the resin, having fixed the traces of cysteamine or cystamine not having reacted, is removed by filtration. To reduce the disulfide optionally present, there are added to the stirred filtrate, 10 g of sulfonic resin and 3 g of zinc powder. After 3 hours the mixture is filtered and the filtrate is concentrated under reduced pressure. After drying, 5 g of N-(2-mercapto ethyl) succinimide are obtained in the form of a white powder whose melting point is 45° C.

The NMR $^1$H and $^{13}$C spectra conform to the expected structure.

Elemental analysis: $C_6H_{11}NO_3S$:

Calculated: C: 45.27, H: 5.70, N: 8.80, O: 20.10, S: 20.14.

Found: C: 45.32, H: 5.72, N: 8.64, O: 20.10, S: 20.14.

(b) Starting with N-(2-mercapto ethyl) succinamic acid

In a 100 cm$^3$ reactor fitted with a water separator (Dean Stark) there is heated to a temperature of 140° C. a mixture, stirred under an inert atmosphere, of 20 g of N-(2-mercapto ethyl) succinamic acid in 50 cm$^3$ of xylene. After about 5 hours of reaction, the theoretical amount of water (2 cm$^3$) is removed. The xylene is then distilled under reduced pressure. The crude product is dried and 18 g of a pasty product are obtained which slowly crystallizes at ambient temperature, its characteristics being the same as those of the product prepared following the procedures in section (a) immediately above.

EXAMPLE III

Preparation of bis [N-(3-carboxy propionyl) N-ethyl]disulfide

A solution of 3.7 g of cysteamine and 2 g of succinic anhydride in 80 cm$^3$ of ethanol is heated with stirring to the boiling temperature of ethanol for 10 hours, the time at the end of which all the anhydride is transformed. The mixture is left overnight and the next day, at ambient temperature, air is bubbled into the middle of the solution until all of the thiol is transformed into disulfide. The mixture is concentrated to a half volume and then cooled to 0° C. The crystallized disulfide is filtered and dried. 2 g of bis[N-(3-carboxy propionyl)N-ethyl]-disulfide are obtained in the form of a white powder whose melting point is 141° C.

Elemental analysis: $C_{12}H_{20}N_2O_6S_2$:

Calculated: C: 40.89, H: 5.72, N: 7.95, O: 27.24, S: 18.20.

Found: C: 40.64, H: 5.77, N: 7.95, O: 27.3, S: 18.00.

EXAMPLE IV

Preparation of bis[(N-ethyl succinimide)]disulfide 15.9 g (0.1 mole) of N-(2-mercapto ethyl) succinimide, described in Example II, are disclosed in about 200 cm$^3$ of ethanol and 200 cm$^3$ of water. The solution is cooled to a temperature between 15° and 20° C., and a few drops of 20% ammonia are added to render the pH alkaline. Slowly H$_2$O$_2$ at 110 volumes is added until total transformation of the thiol into disulfide (dosage with iodine)

The solution is clarified by filtration on fritted glass and then concentrated under reduced pressure to about 100 cm$^3$. After cooling to 0° C., the white solid is filtered and then dissolved again in a minimum of ethanol. The solution is filtered and then concentrated under a vacuum until the onset of crystallization. It is then cooled to ±5° C., the resulting crystals are filtered and dried under a vacuum at 60°–70° C. 12.8 g of bis(N-ethyl succinimide) disulfide are obtained in the form of a white solid having a melting point of 119° C.

The NMR $^1$H 80 MHz spectrum conforms to the expected structure.

| Elemental analysis: $C_{12}H_{16}N_2O_4S_2$ | | | | |
|---|---|---|---|---|
| C | H | N | O | S |
| Calculated: 44.55 | 5.10 | 8.85 | 20.23 | 20.27 |
| Found: 45.66 | 5.03 | 8.78 | 20.40 | 20.21 |

EXAMPLE V

Preparation of N-(2-mercapto ethyl) hexahydrophthalamic acid

To a solution of 7.72 g (0.1 mole) of cysteamine in 40 cm$^3$ of methanol, maintained under an inert atmosphere and cooled to a temperature between 0° and 5° C., there are added, by portions, 15.43 g (0.1 mole) of hexahydrophthalic anhydride. After 7 hours of stirring at this temperature, there remains only traces of the starting cysteamine. The solution is evaporated to dryness under reduced pressure at ambient temperature. 23 g of N-(2-mercapto ethyl) hexahydrophthalamic acid are obtained in the form of a colorless oil.

The NMR $^1$H 80 MHz spectrum corresponds to the expected structure.

EXAMPLE VI

Preparation of N-(2-mercapto ethyl) hexahydrophthalimide

In a reaction fitted with a Dean-Stark, there are introduced under an inert gas 15.43 g (0.2 mole) of cysteamine, 100 cm$^3$ of toluene and 30.83 g (0.2 mole) of hexahydrophthalic anhydride. The mixture is heated to reflux with stirring and with distillation of the water formed. After 4 hours of reflux, the reaction is complete. The reaction medium is evaporated to dryness under reduced pressure and the resulting white solid is purified by recrystallization in ethyl acetate. After drying under a vacuum at 70° C., 37.5 g of N-(2-mercapto ethyl) hexahydrophthalimide are obtained in the form of a white solid having a melting point of 79°–80° C.

The NMR $^1$H 80 MHz spectrum conforms to the expected structure.

| Elemental analysis: $C_{10}H_{15}NO_2S$ | | | | |
|---|---|---|---|---|
| C | H | N | O | S |
| Calculated: 56.31 | 7.09 | 6.57 | 15.00 | 15.03 |
| Found: 56.07 | 7.11 | 6.39 | 15.02 | 14.93 |

EXAMPLE VII

Preparation of N-(3-mercapto propyl glutaramic acid

To a solution of 6.84 g (0.075 mole) of 3-mercapto propyl amine (homocysteamine) in 20 cm$^3$ of methanol, maintained under an inert atmosphere and stirred at ambient temperature, there are added, by portions, 8.56 g (0.075 mole) of glutaric anhydride while maintaining the temperature of the reaction mixture lower than 40° C. After stirring for 6 hours 30 minutes the reaction is complete. The solution is evaporated to dryness under reduced pressure. The product is then dried under a vacuum at a temperature lower than 60° C. and 19.5 g of N-(3-mercapto propyl) glutaramic acid are obtained in the form of a colorless oil.

The NMR $^1$H 80 MHz spectrum conforms to the expected structure.

EXAMPLES OF COMPOSITIONS

Example 1

In accordance with the invention, a reducing composition for the permanent deformation of hair is prepared by proceeding to mix the following substances:

| | |
|---|---|
| N-(2-mercapto ethyl) succinamic acid | 18 g |
| Monoethanolamine, sufficient for pH = 8.5 | |
| Oleocetyl dimethyl hydroxyethyl ammonium chloride, sold under the trade name "CHIMEXANE CI" by Chimex | 0.3 g |
| Perfume, sufficient amount | |
| Preservative, sufficient amount | |
| Demineralized water, sufficient amount for | 100 g |

This composition is applied to wet hair previously rolled up on hair setting rollers. After having let the composition act on the hair for about 15 minutes, the hair is thoroughly rinsed with water and then the following oxidation composition is applied:

| | |
|---|---|
| H$_2$O$_2$, sufficient for 8 volumes | |
| Stabilizer, sufficient amount | |
| Lauryl dimethyl amine oxide | 0.7 g |
| Perfume, sufficient amount | |
| Lactic acid, sufficient for pH = 3.0 | |
| Demineralized water, sufficient amount for | 100 g |

| | |
|---|---|
| H$_2$O$_2$, sufficient for 8 volumes | |
| Stabilizer, sufficient amount | |
| Perfume, sufficient amount | |
| Citric acid, sufficient for pH = 3.5 | |
| Demineralized water, sufficient amount for | 100 g |

Example 2

In accordance with the same operating procedures set forth in Example 1, a permanent deformation of hair is effected using the following reducing and oxidizing compositions

| A. Reducing composition | |
|---|---|
| N-(2-mercapto ethyl) succinamic acid | 13 g |
| bis[N-(3-carboxy propionyl) N-ethyl] disulfide | 5 g |
| Monoethanolamine, sufficient for pH = 9.0 | |
| Cocoylamidopropyl betaine with copra monoglyceride, sold under the trade name "TEGOBETAINE HS" by Goldschmidt | 0.3 g |
| Perfume, sufficient amount | |
| Preservative, sufficient amount | |
| Demineralized water, sufficient amount for | 100 g |
| B. Oxidation Composition | |
| Sodium bromate | 8 g |
| Triethanolamine, sufficient for pH = 8.0 | |
| Hydrated monosodium phosphate (12H$_2$O) | 0.3 g |
| Hydrated trisodium phosphate (2H$_2$O) | 0.5 g |
| Cocoylamidopropyl betaine with copra monoglyceride, sold under the trade name "TEGOBETAINE HS" by Goldschmidt | 1 g |
| Demineralized water, sufficient amount for | 100 g |

Example 3

| A. Reducing composition | |
|---|---|
| N-(2-mercapto ethyl) succinimide | 10 g |
| Monoethanolamine, sufficient for pH = 9.0 | |
| Oleocetyl dimethyl hydroxyethyl ammonium chloride, sold under the trade name "CHIMEXANE CI" by Chimex | 0.3 g |
| Perfume, sufficient amount | |
| Preservative, sufficient amount | |
| Demineralized water, sufficient amount for | 100 g |
| B. Oxidation composition | |
| H$_2$O$_2$ at 200 volumes | 4.8 g |
| 8-hydroxy quinolein sulfate | 0.01 g |
| Phenacetin | 0.05 g |
| Citric acid, sufficient for pH = 3.0 | |
| Perfume, sufficient amount | |
| Demineralized water, sufficient amount for | 100 g |

Example 4

| A. Reducing Composition | |
|---|---|
| N-(2-mercapto ethyl) succinamic acid | 6 g |
| N-(2-mercapto ethyl) succinimide | 4 g |
| bis[N-(3-carboxy propionyl)N-ethyl] disulfide | 2 g |
| Monoethanolamine, sufficient for pH = 8.7 | |
| Cetyl trimethyl ammonium chloride | 1.0 g |
| Perfume, sufficient amount | |
| Preservative, sufficient amount | |
| Demineralized water, sufficient amount for | 100 g |
| B. Oxidation composition | |
| H$_2$O$_2$, sufficient amount for 8 volumes | |
| Mixture of sodium lauryl and myristyl ether sulfate (in a 70/30 ratio etherified with 2.2 moles of ethylene oxide), sold under the trade name "SIPON AOS 225" by Henkel | 3.5 g |
| Stabilizer, sufficient amount | |
| Perfume, sufficient amount | |
| Citric acid, sufficient for pH = 3.0 | |
| Demineralized water, sufficient amount for | 100 g |

Example 5

| A. Reducing composition | |
|---|---|
| N-(2-mercapto ethyl) hexahydrophthalamic acid | 11.5 g |
| Monoethanolamine, sufficient for pH = 9.0 | |
| Oleocetyl dimethyl hydroxyethyl ammonium chloride, sold under the trade name "CHIMEXANE CI" by Chimex | 0.3 g |
| Perfume, sufficient amount | |
| Preservative, sufficient amount | |
| Demineralized water, sufficient amount for | 100 g |
| B. Oxidation composition | |
| H$_2$O$_2$ at 200 volumes | 4.8 g |
| 8-hydroxy quinolein sulfate | 0.01 g |
| Phenacetin | 0.05 g |
| Citric acid, sufficient for pH = 3.0 | |
| Perfume, sufficient amount | |
| Demineralized water, sufficient amount for | 100 g |

Example 6

| A. Reducing composition | |
|---|---|
| N-(2-mercapto ethyl) hexahydrophthalimide | 16 g |
| Monoethanolamine, sufficient for pH = 9.0 | |
| Oleocetyl dimethyl hydroxyethyl ammonium chloride, sold under the trade name | 0.3 g |

-continued

| | |
|---|---|
| "CHIMEXANE CI", by Chimex | |
| Perfume, sufficient amount | |
| Preservative, sufficient amount | |
| Demineralized water, sufficient amount for | 100 g |
| B. Oxidation composition | |
| H₂O₂ at 200 volumes | 4.8 g |
| 8-hydroxy quinolein sulfate | 0.01 g |
| Phenacetin | 0.05 g |
| Citric acid, sufficient for pH = 3.0 | |
| Perfume, sufficient amount | |
| Demineralized water, sufficient amount for | 100 g |

Example 7

| | |
|---|---|
| A. Reducing composition | |
| N-(2-mercapto ethyl) succinamic acid | 9.3 g |
| Copolymer of N-vinylpyrrolidone/dimethyl-aminoethyl methacrylate in 20 weight percent aqueous solution, sold by GAF under the trade name "COPOLYMER 845" | 1 g |
| Ammonia, sufficient amount for pH = 9.0 | |
| Perfume, sufficient | |
| Dye, sufficient | |
| Preservative, sufficient | |
| Water, sufficient amount for | 100 g |
| B. Oxidation composition | |
| H₂O₂ at 200 volumes | 4.8 g |
| Citric acid, sufficient for pH = 3.0 | |
| Perfume, sufficient | |
| Demineralized water, sufficient amount for | 100 g |

Example 8

| | |
|---|---|
| A. Reducing composition | |
| Cysteine | 2.50 g |
| N-(2-mercapto ethyl) succinamic acid | 3.63 g |
| Oleocetyl dimethyl hydroxyethyl ammonium chloride, sold under the trade name "CHIMEXANE CI" by Chimex | 1.30 g |
| Monoethanolamine, sufficient for pH = 9 | |
| Demineralized water, sufficient amount for | 100 g |
| B. Oxidation composition | |
| H₂O₂ at 200 volumes | 4.8 g |
| Citric acid, sufficient for pH = 3.0 | |
| Perfume, sufficient amount | |
| Demineralized water, sufficient amount for | 100 g |

Example 9

| | |
|---|---|
| A. Reducing composition | |
| Cysteine | 1.34 g |
| N-(2-mercapto ethyl) succinamic acid | 5.31 g |
| Oleocetyl dimethyl hydroxyethyl ammonium chloride, sold under the trade name "CHIMEXANE CI" by Chimex | 1.30 g |
| Monoethanolamine, sufficient for pH = 9 | |
| Demineralized water, sufficient amount for | 100 g |
| B. Oxidation composition | |
| H₂O₂ at 200 volumes | 4.8 g |
| Citric acid, sufficient for pH = 3.0 | |
| Perfume, sufficient amount | |
| Demineralized water, sufficient amount for | 100 g |

Example 10

| | |
|---|---|
| A. Reducing composition | |
| Cysteine | 5.0 g |
| N-(2-mercapto ethyl) succinamic acid | 3.63 g |

-continued

| | |
|---|---|
| Oleocetyl dimethyl hydroxyethyl ammonium chloride, sold under the trade name "CHIMEXANE CI" by Chimex | 1.30 g |
| Monoethanolamine, sufficient for pH = 9 | |
| Demineralized water, sufficient amount for | 100 g |
| B. Oxidation composition | |
| H₂O₂ at 200 volumes | 4.8 g |
| Citric acid, sufficient for pH = 3.0 | |
| Perfume, sufficient amount | |
| Demineralized water, sufficient amount for | 100 g |

Example 11

| | |
|---|---|
| A. Reducing composition | |
| Cysteamine hydrochloride | 2.77 g |
| N-(2-mercapto ethyl) succinamic acid | 7.26 g |
| Oleocetyl dimethyl hydroxyethyl ammonium chloride, sold under the trade name "CHIMEXANE CI" by Chimex | 1.30 g |
| Monoethanolamine, sufficient for pH = 9 | |
| Demineralized water, sufficient amount for | 100 g |
| B. Oxidation composition | |
| H₂O₂ at 200 volumes | 4.8 g |
| Citric acid, sufficient for pH = 3.0 | |
| Perfume, sufficient amount | |
| Demineralized water, sufficient amount for | 100 g |

We claim:
1. A cosmetic reducing composition for the first stage of an operation for the permanent deformation of hair comprising in a cosmetically acceptable vehicle, as a reducing agent, at least one derivative of N-(mercapto alkyl) succinamic acid or of N-(mercapto alkyl) succinimide, both having the formula

$$HS-(CH_2)_n-\underset{R_1}{N}-\overset{O}{\underset{\|}{C}}-A-\overset{O}{\underset{\|}{C}}-R_2 \qquad (I)$$

wherein
n is s 2 or 3,
A represents a divalent radical selected from (i) $-(CH_2)_m-$, wherein m is 2 or 3, (ii) $-\underset{R_3}{CH}-\underset{R_4}{CH}-$, wherein $R_3$ and $R_4$, each independently, represent alkyl having 1-4 carbon atoms, or $R_3$ and $R_4$ together with adjacent carbon atoms form a cyclohexane ring, and (iii) $-\underset{R_5}{C}=\underset{R_6}{C}-$, wherein $R_5$ and $R_6$, each independently, represent hydrogen, alkyl having 1-4 carbon atoms, or $R_5$ and $R_6$ together with the adjacent carbon atoms form a benzene ring,
$R_1$ represents hydrogen,
$R_2$ represents hydroxy, or
$R_1$ and $R_2$ taken together form a simple bond,
and the salts of an organic or mineral base of the said compounds in free acid form, said salts being ammonium, a secondary or tertiary amine, an alkali metal or an alkaline earth metal salt.

2. The composition of claim 1 where in formula (I) $R_1$ represents hydrogen and $R_2$ represents hydroxy, the said compound is selected from
N-(2-mercapto ethyl) succinamic acid,
N-(3-mercapto propyl) succinamic acid,
N-(2-mercapto ethyl) hexahydrophthalamic acid,
N-(3-mercapto propyl) hexahydrophthalamic acid,
N-(2-mercapto ethyl) phthalamic acid,
N-(3-mercapto propyl) phthalamic acid,
N-(2-mercapto ethyl) glutaramic acid,
N-(3-mercapto propyl) glutaramic acid and
N-(2-mercapto ethyl) maleamic acid.

3. The composition of claim 1 wherein when in formula (I) $R_1$ and $R_2$ taken together form a simple bond, said compound is selected from:
N-(2-mercapto ethyl) succinimide,
N-(3-mercapto propyl) succinimide,
N-(2-mercapto ethyl) glutarimide,
N-(3-mercapto propyl) glutarimide,
N-(2-mercapto ethyl) hexahydrophthalimide and
N-(3-mercapto propyl) hexahydrophthalimide.

4. The composition of claim 1 wherein said compound of formula (I) is present in an amount ranging from 2 to 20 percent by weight based on the total weight of said composition.

5. The composition of claim 1 wherein said compound of formula I is present in an amount ranging from 5 to 10 percent by weight based on the total weight of said composition.

6. The composition of claim 1 having a pH ranging from 4.5-11 obtained using an alkaline agent selected from ammonia, monoethanolamine, diethanolamine, triethanolamine, an alkaline or ammonium carbonate or bicarbonate, an alkaline hydroxide, or using an acidifying agent selected from hydrochloric acid, acetic acid, lactic acid, oxalic acid or boric acid.

7. The composition of claim 6 wherein said pH ranges from 6 to 10.

8. The composition of claim 1 which also contains at least one other reducing agent selected from thioglycolic acid, glycerol mono-thioglycolate, glycol mono-thioglycolate, cysteamine and its $C_1$-$C_4$ acylated derivatives, cysteine, N-acetyl-cysteine, N-mercapto alkylamides of sugars, β-mercaptopropionic acid and its derivatives, thiolactic acid, thiomalic acid,, pantetheine, thioglycerol, an alkali metal or alkaline earth metal sulfite or bisulfite, N-(mercapto alkyl) ω-hydroxylamides, N-mono or N,N,-dialkylmercapto 4-butyramides and amino mercapto alkylamides.

9. The composition of claim 1 which also contains at least one of a cationic polymer, a softening agent, a protein hydrolyzate, a wax, an opacifying agent, a perfume, a dye, a nonionic or cationic surfactant, a treating agent or a penetration agent.

10. The composition of claim 1 which also contains at least one disulfide, said composition being self-neutralizing.

11. The composition of claim 10 wherein said disulfide is selected from dithioglycolic acid, dithioglycerol, cystamine, N,N-diacetyl cystamine, cystine, pantetheine, the disulfides of N-(mercapto alkyl) TM-hydroxy alkylamides, the disulfides of N-mono or N,N-dialkylmercapto 4-butyramides and the disulfides of aminomercapto-alkylamides.

12. The composition of claim 10 wherein said disulfide is a disulfide of the compound of formula (I) and has the formula

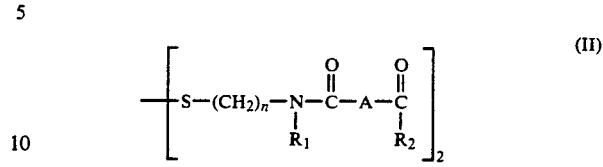

wherein
n is 2 or 3,
a represents a divalent radical selected from (i) $-(CH_2)_m-$, wherein m is 2 or 3,

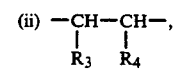

wherein $R_3$ and $R_4$, each independently, represent alkyl having 1-4 carbon atoms, or $R_3$ and $R_4$ together with the adjacent carbon atoms form a cyclohexane ring, and

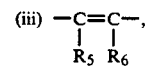

wherein $R_5$ and $R_6$, each independently, represent hydrogen, alkyl having 1-4 carbon atoms, or $R_5$ and $R_6$ together with the adjacent carbon atoms form a benzene ring,
$R_1$ represents hydrogen,
$R_2$ represents hydroxy, or
$R_1$ and $R_2$ taken together form a simple bond.

13. The composition of claim 12 wherein said disulfide of formula (II) is selected from
bis[N-(3-carboxy propionyl)N-ethyl]disulfide,
bis[N-(2-carboxy cyclohexane carbonyl)N-ethyl]disulfide and
bis[N-ethyl succinimide] disulfide.

14. The composition of claim 10 wherein said disulfide is present in a molar proportion with respect to the compound of formula (I) ranging from 0.5 to 2.5.

15. The composition of claim 10 wherein said disulfide is present in a molar proportion with respect to the compound of formula (I) ranging from 1 to 2.

16. A process for the permanent deformation of hair comprising, in a first stage, reducing the disulfide bonds of keratin by applying to the hair a reducing composition and then in a second stage reforming the said bonds by applying to the hair in oxidation composition, the said reducing composition being the cosmetic composition of claim 1.

17. The process of claim 16 where in said first stage, said reducing composition is permitted to remain in contact with the hair for a period of time ranging from 5 to 60 minutes.

18. A compound having the formula

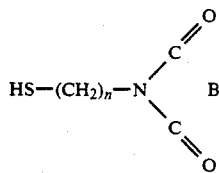

(III)

wherein
n is 2 or 3, and
B represents a divalent radical selected from the group consisting of
(i) —(CH$_2$)$_3$—
(ii) 1,2-cyclohexylidene, and
(iii) —CH=CH— when in this latter case n is 3, and their corresponding disulfides.

19. A compound having the formula

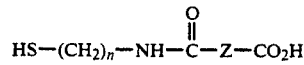

(IV)

wherein
n is 2 or 3,
(a) when n is 2, Z represents 1,2-cyclohexylidene and
(b) when n is 3, Z is a divalent radical selected from the group consisting of
(i) —(CH$_2$)$_m$— wherein m is 2 or 3,
(ii) —CH=CH—,
(iii) 1,2-cyclohexylidene, and
(iv) O-phenylene,
and the corresponding disulfides, as well as the corresponding disulfide when n is 2 and Z represents o-phenylene.

* * * * *